(12) United States Patent
Weil et al.

(10) Patent No.: US 7,570,993 B2
(45) Date of Patent: Aug. 4, 2009

(54) ENHANCED CPR PROTECTOR SYSTEM

(75) Inventors: Max Harry Weil, Northbrook, IL (US);
Wanchun Tang, Palm Desert, CA (US);
Joe Bisera, Camarillo, CA (US)

(73) Assignee: The Institute of Critical Care Medicine, Rancho Mirage, CA (US)

( * ) Notice: Subject to any disclaimer, the term of this patent is extended or adjusted under 35 U.S.C. 154(b) by 1891 days.

(21) Appl. No.: 09/953,032

(22) Filed: Sep. 12, 2001

(65) Prior Publication Data

US 2002/0026229 A1 Feb. 28, 2002

Related U.S. Application Data

(63) Continuation-in-part of application No. 09/472,303, filed on Dec. 27, 1999, now abandoned.

(51) Int. Cl.
*A61N 1/39* (2006.01)
(52) U.S. Cl. .......................................................... 607/5
(58) Field of Classification Search .................. 607/3–5, 607/115, 142, 152
See application file for complete search history.

(56) References Cited

U.S. PATENT DOCUMENTS

| | | | | | |
|---|---|---|---|---|---|
| 4,708,149 | A | * | 11/1987 | Axelgaard et al. | 607/152 |
| 4,776,350 | A | * | 10/1988 | Grossman et al. | 607/152 |
| 5,824,033 | A | * | 10/1998 | Ferrari | 607/142 |
| 5,957,856 | A | | 9/1999 | Weil et al. | |

OTHER PUBLICATIONS

Insulation, Electric (Properties) vol. 13 p. 557.*
Dictionary p. 1523.*
Insulation, Electric (Wire and Cable) vol. 13 p. 565.*

* cited by examiner

*Primary Examiner*—George R Evanisko
(74) *Attorney, Agent, or Firm*—Leon D. Rosen

(57) ABSTRACT

Apparatus is provided for treatment of a victim to reverse cardiac arrest by chest compression and by electrical defibrillation through electrodes applied to the chest area of the victim. The apparatus includes a dielectric layer which is placed on the victim to electrically isolate the rescuer who is performing chest compressions. The protective sheet includes a layer of electrically conductive material sandwiched between two dielectric layers to electrically isolate the rescuer. The sandwiched conductive layer is connected to a location on the body of the victim that is spaced a plurality of inches from each of the electrodes.

3 Claims, 6 Drawing Sheets

ENHANCED CPR PROTECTOR SYSTEM

CROSS-REFERENCE TO RELATED APPLICATION

This is a continuation-in-part of U.S. patent application Ser. No. 09/472,303 filed Dec. 27, 1999 now abandoned.

BACKGROUND OF THE INVENTION

Automatic defibrillators use a pair of electrodes applied to the chest of the victim for sensing EKG (electrocardiograph) signals from the victim. These electrodes are also used to deliver a high voltage defibrillator pulse to the victim when electrocardiograph interpretation permits discharge, either by advising the rescuer to deliver the shock or by automatic delivery of the shock. Precordial compression in the area of the breastbone helps blood circulation and breathing. The rescuer is provided with a verbal warning such as "step back" prior to delivering the shock to protect the rescuer from a high voltage defibrillator shock. In the present invention we avoid the need for discontinuance of precordial compression by the rescuer, resulting in a better outcome of the rescue effort.

Applicants' previous patent application Ser. No. 09/217, 008 filed Dec. 21,1998, describes a sheet of insulation material that can be applied to the victim to protect the rescuer from defibrillator shocks. While the rescuer is partially protected, it is found that the rescuer feels highly annoying moderate shocks when the patient is defibrillated. Apparatus that provides more complete insulation would be useful.

In our earlier U.S. Pat. No. 5,957,856 and patent application Ser. No. 09/385,537 filed Aug. 30, 1999, a system is provided for evaluating the likelihood that a defibrillator shock will successfully restore spontaneous circulation, based on analysis of the patient's electrocardiogram. If a shock is indicated on the basis of the analysis, the shock may be applied through electrodes on the patient's chest. It is desirable to provide a favorable voltage level of the delivered shock to minimize injury to the heart of the patient by avoiding excessive voltage and yet deliver adequate current for successful restoration of circulation.

When the rescuer applies chest compressions to the patient, he/she must supply sufficiently vigorous compression to cause blood to circulate while limiting the force applied to avoid injury to the patient. Apparatus to guide the rescuer would be desirable.

SUMMARY OF THE INVENTION

In accordance with one embodiment of the present invention, a sheet is provided for better protecting a rescuer who is applying compressions to a patient's chest, when high voltage pulses are being applied to the patient through electrodes. The protective sheet includes a pair of layers of dielectric material, and a conductive layer of electrically conductive material lying between the dielectric layers. The conductive layer is connected to the patient at a location spaced more than one inch from the electrodes through which high voltage pulses are applied. Applicant finds this reduces the amplitude of secondary shock applied to the rescuer when a defibrillating shock is applied to the patient.

In another embodiment, a sensor is placed on the protective sheet at a location that is to lie over the middle of the lower chest area of the patient that is the site of chest compression. The sensor may be an accelerometer or other methods may be used to determine depth of compression. At the same time, the depth of compression can be related to concurrent measurements indicating effectiveness of compression such as blood pressure and carbon dioxide measurements. A circuit is integrated with the accelerometer for producing a signal that guides the vigor of chest compression. That is, the circuit can indicate the depth of compression of the patient's chest and the acceleration that was applied to the patient and indicate whether these levels are too high or too low.

The sheet can be provided with pockets which accommodate other resuscitative supplies including breathing devices, disease barriers for mouth to mouth transmission, and a carbon dioxide sensor for estimating cardiac output.

The novel features of the invention are set forth with particularity in the appended claims. The invention will be best understood from the following description when read in conjunction with the accompanying drawings.

BRIEF DESCRIPTION OF THE DRAWINGS

FIG. 13 is a graph showing variation in depth with time resulting from the acceleration profile of FIG. 12.

DESCRIPTION OF THE PREFERRED EMBODIMENTS

Figure 6A:
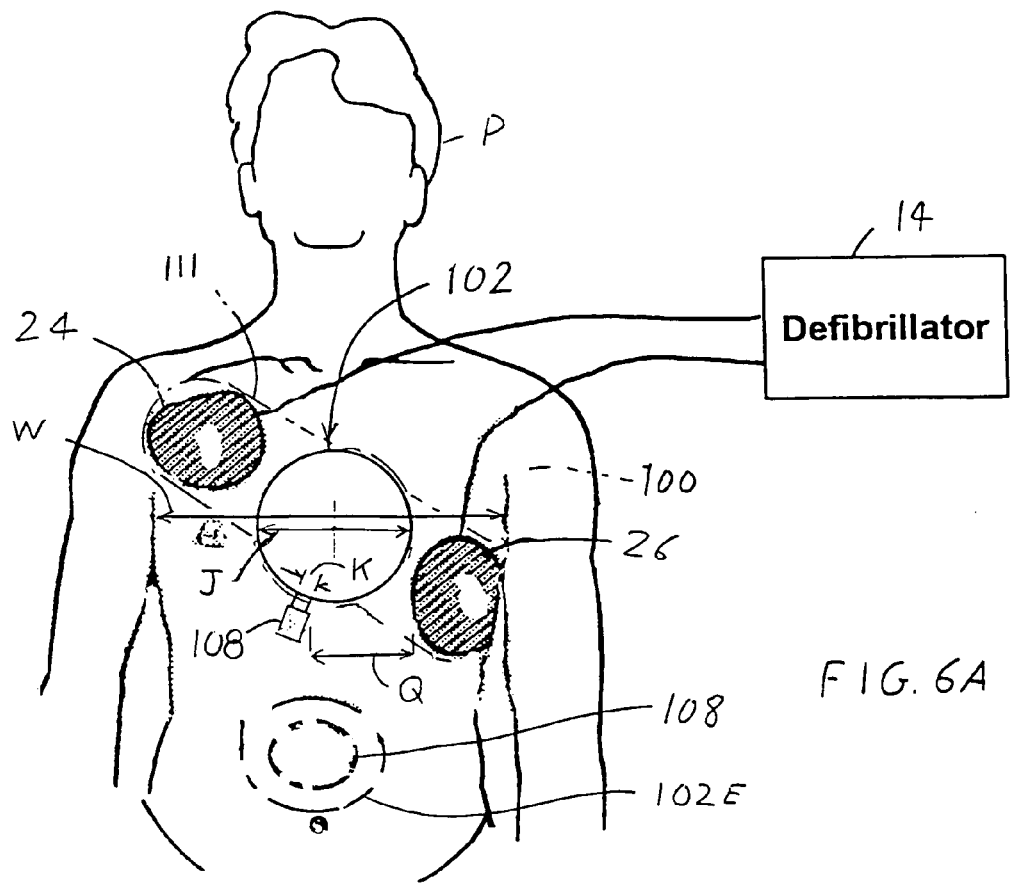
FIG. 6A is a plan view of the protective sheet of FIG. 6 and a defibrillator connected thereto.

1. Detailed Description of One Feature:

FIG. 6A shows a defibrillator 14 connected to electrodes 24, 26 on the chest area of a victim or patient P. A flexible protective sheet 102 is placed over the sternum area of the patient, which is the middle of the chest. A rescuer can apply repeated compressions to the patient's chest by pressing his hands directly against the sheet 102. The rescuer takes care not to directly touch the skin of the patient, at least when a warning is giving that a voltage pulse is about to be applied.

Figure 6:
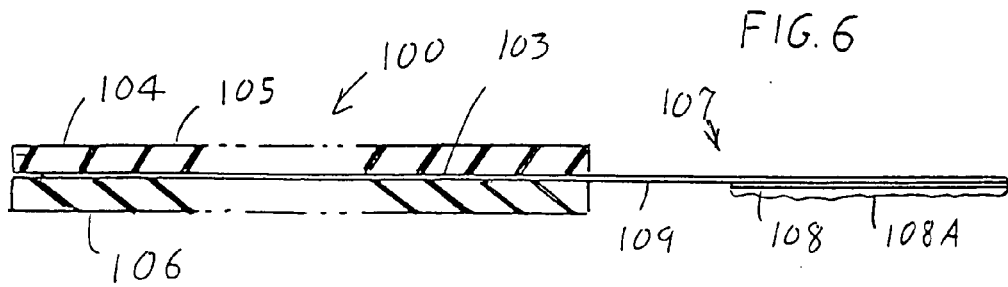
FIG. 6 is a partial sectional view of a protective sheet constructed in accordance with another embodiment of the invention.

The protective sheet has a construction such as shown in FIG. 6, with an electrically conductive layer 103 sandwiched between two electrically insulative layers 104, 106. A connector 107, which may be an extension of the conductive layer or a separate part, has a skin-contacting terminal part 108. The terminal part of the connector connects the conductive layer 103 to the patient. FIG. 6A shows that the location of the terminal part 108 is spaced a distance Q of at least 1.5 inches from each of the electrodes 24, 26 (or at least the electrode with the high voltage). The upper surface 105 of the protective sheet is devoid of an exposed electrical conductor that is connected to the patient, to avoid a shock to the rescuer who accidently touches such conductor during defibrillation. The conductive layer 103 preferably extends under a majority of the upper area of the protective sheet, more preferably over 75% of the upper area, and most preferably substantially the entire area (at least 95%). The body of the patient is a potential (voltage) source, whose potential is lower than that of the short duration defibrillation pulse at locations spaced from the electrodes.

Applicant finds that the presence of the electrically conductive layer 103 connected to the patient, greatly reduces the shock felt by the rescuer who is pressing on the upper face of the protective sheet when a high voltage pulse is applied. Instead of a voltage of perhaps 200 volts being felt by the rescuer when 3000 volts is applied between the electrodes, a voltage of perhaps 50 volts is felt. A shock at 50 volts at very low current, is usually not highly annoying to the rescuer. This allows the rescuer to continue chest compressions while defibrillating voltage pulses are applied to the patient through the electrodes. Otherwise, the rescuer might stop for perhaps 5 seconds every time a warning of a pulse is given and until the pulse has been applied, which decreases the possibility of patient recovery.

The skin of the patient at the electrodes 24, 26 (or at least the electrode that applies a high voltage) is commonly at least one thousand volts. The patient's body has a moderate resistance and capacitance, and the voltage (above or below ground potential) of the patient's skin at locations progressively further from the electrodes is generally progressively lower. Thus, the patient's skin at locations spaced from the electrodes (or at least the one with a high voltage) serves as a potential source whose voltage varies by less than the voltage at the electrode voltage during defibrillation. If the maximum voltage, or potential, of the conductive layer 103 is kept only moderately above ground, such as less than one-tenth the maximum voltage of the highest-voltage electrode, then a rescuer pressing against the upper surface 105 of the protective sheet, will experience a lower voltage shock. In the above example where the defibrillating pulse maximum is 3000 volts, the connector 107 is connected to a body location at 600 volts, the conductive layer voltage may rise to 250 volts, and the upper surface of the protective sheet may rise to perhaps 50 volts. In the absence of the conductive layer, the rescuer might instead be subjected to perhaps 200 volts.

The maximum voltage of the conductive layer 103 is minimized by placing most of the layer away from the electrodes (where the skin voltage is lower), and especially by connecting the conductor 107 to a skin location away from the electrodes. Applicant prefers to place the terminal part 108 of the connector more than 1.5 inches away from each of the electrodes, preferably at least two inches away, more preferably at least three inches away, and most preferably at least about four inches away. A conductive adhesive at 108A such as a gel, connects the termination part 108 to the skin. The conductor 109 that connects an edge of the conductive layer to the termination part 108 that lies against the patient's skin, has a width K no more than 25% of the width J of the conductive layer. Applicant believes that the moderate resistance (e.g. 0.5 ohm) of the conductor 109 between the terminal part 108 and the conductive layer 103 results in a slower charging of the conductive layer, and a slower increase in the voltage of the electrically conductive sheet. As a result, the voltage of the sheet does not rise very high during a period of perhaps five milliseconds when the defibrillating pulse has a high voltage.

FIG. 6A shows that the width W of an average chest at the sternum is about 13 inches. In FIG. 6A, the terminal contact end 108 of the connector is spaced a distance Q of 3.9 inches from the electrode 26 and about 4.2 inches from electrode 24. A greater distance is desirable, but at least about 4 inches is adequate, and applicant wishes to make the protective sheet compact.

It is possible to attach defibrillation electrodes to the protective sheet, but such electrodes must not touch the conductive sandwiched sheet 103. It is possible to connect the conductive sheet to an Earth-connected ground potential source (e.g. a pipe or a ground terminal of a home electrical outlet) but this can be difficult for a rescuer to quickly perform. It is possible to place the terminal part 108 directly under the protective sheet. In any case, applicant applies a conductive gel to the terminal part 108 before attaching the terminal part to the skin. In one example, the protective sheet 102 is a circle of about 6 inches diameter J (15.25 cm) and an area of 25 square inches (195 cm$^2$). If the rescuer can be sure that one of the electrodes is maintained at ground, then, the conductive sheet can be connected to that electrode. It is possible to provide a protective sheet with built in electrodes, as shown at 111 in FIG. 6A.

Figure 1:
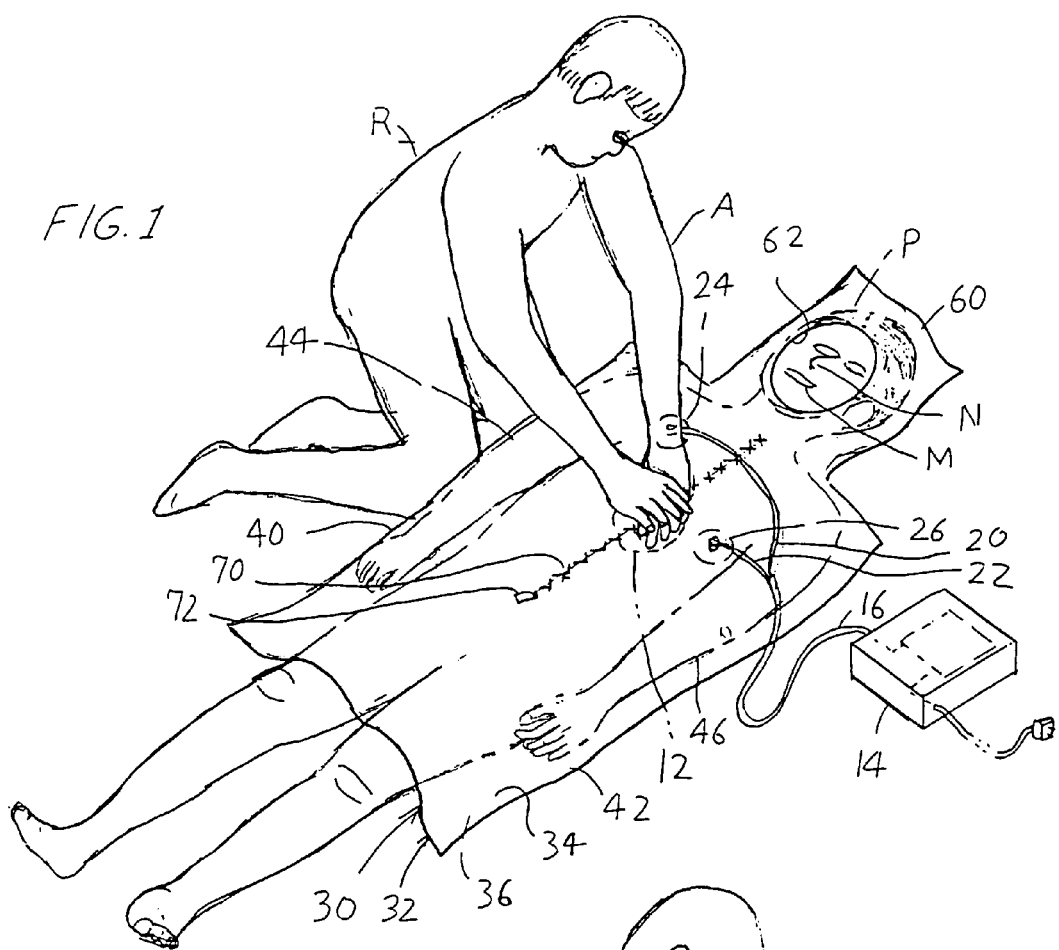
FIG. 1 is an isometric view of a victim and rescuer, and of apparatus of the present invention.
Figure 5:
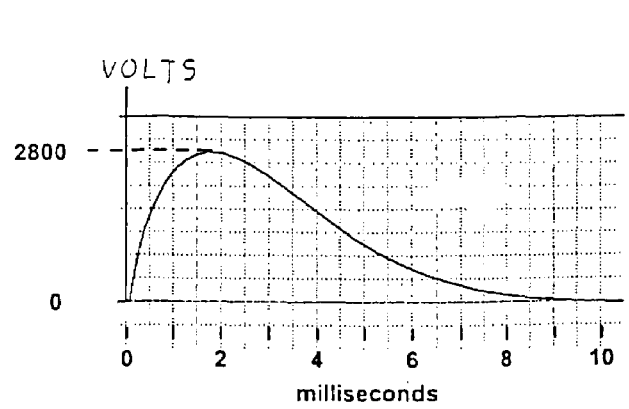
FIG. 5 is a graph showing variation in voltage with time of a monophasic defibrillation pulse applied by the defibrillator of FIG. 1 to the electrodes of FIG. 1.

2. More Detailed Description of the Invention:

FIG. 1 illustrates a patient P or victim who has symptoms of cardiac arrest, and who is being treated by a rescuer R who is performing precordial compressions, that is, compressions of the lower chest area 12, in conjunction with an automatic defibrillator 14. The defibrillator has a cable 16 with wires 20, 22 having conductors therein, which are connected to first and second electrodes 24, 26. The electrodes are applied to the chest of the victim at predetermined locations. The rescuer applies downward forces or compressions to the area 12 of the victim and also may blow air into the mouth M of the victim by mouth-to-mouth resuscitation or through a rubber bellows or breathing valve. The automatic defibrillator receives EKG (electrocardiogram) signals from the electrodes 24, 26 to analyze the condition of the victim. When the circuitry in the defibrillator determines that an electric shock would be beneficial, the defibrillator sounds an alarm to warn the rescuer and other persons who may be affected. Then a high voltage electric pulse, such as of the type shown in FIG. 5, is applied through the electrodes to the victim. The rescuer must be protected from high voltage shocks that he/she would receive, if there were any physical contact with the victim's body.

Applicant provides an apparatus 30 that includes a sheet 32 of flexible dielectric, or highly insulative, material to electrically shield the rescuer from the victim. The sheet has top and bottom surfaces and prevents the passage of large currents between the opposite surfaces when a voltage of a plurality of hundreds of volts, and usually at least a thousand volts, is applied between the upper and lower faces 34, 36 of the sheet. The sheet covers the lower chest area 12 which is compressed by the rescuer, to protect the rescuer even if he is compressing the victim's chest when the high voltage pulse is applied. The electrodes 24, 26 are attached to the sheet and lie under the lower face of the sheet.

Figure 2:
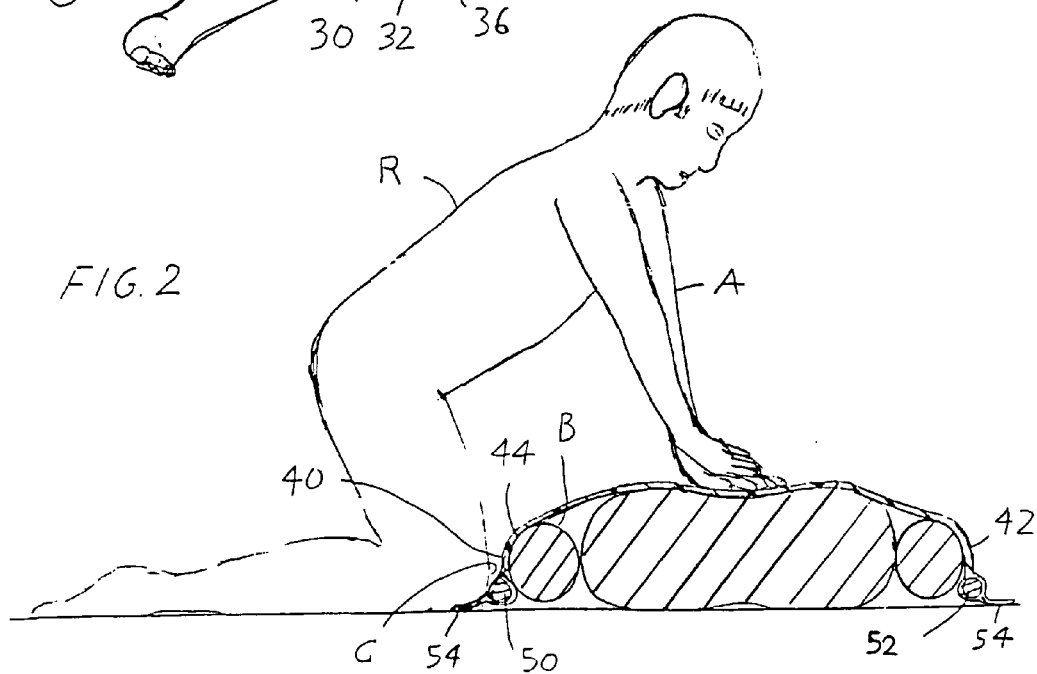
FIG. 2 is a sectional view of the victim and rescuer, and of some of the apparatus of the invention of FIG. 1.

The sheet has opposite side portions 40, 42 that lie beside the opposite sides 44, 46 of the victim in FIGS. 1 and 2, at his arms B. It can be seen from FIG. 2 that the knee area C of the rescuer may lie very close to a first side 44 of the victim. The first side 40 of the sheet covers this side of the victim and preferably extends to the ground. Applicant provides a weight 50, 52 at each side portion of the sheet to assure that it remains draped over the victim's side.

Figure 4:
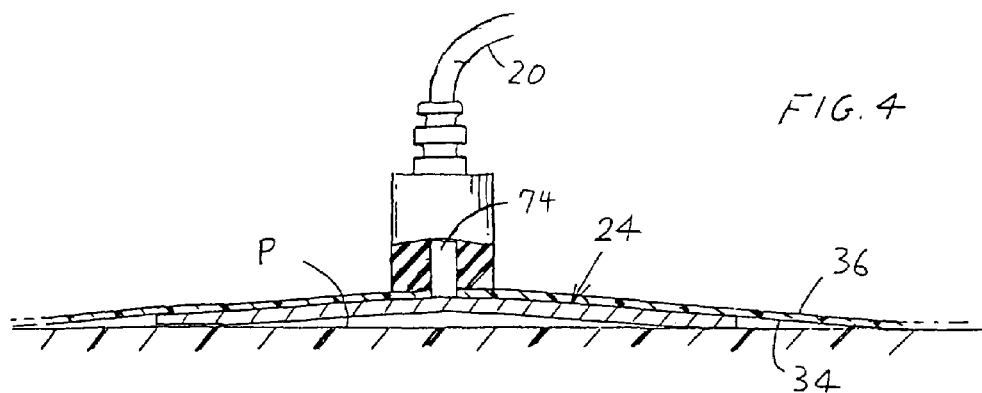
FIG. 4 is a sectional view of the apparatus of FIG. 1, showing an electrode and a portion of the protective sheet.

The sheet has a head part 60 with an opening 62 that uncovers at least the mouth and nose of the victim. The head part gives some protection to a rescuer although it may not be necessary. A slit 70 with a plastic zipper 72 enables easy access to the electrodes. FIG. 4 illustrates one electrode 24 which is pressing against the victim P and which is connected through a conductor 74 of a wire 20 to the defibrillator.

Figure 3:
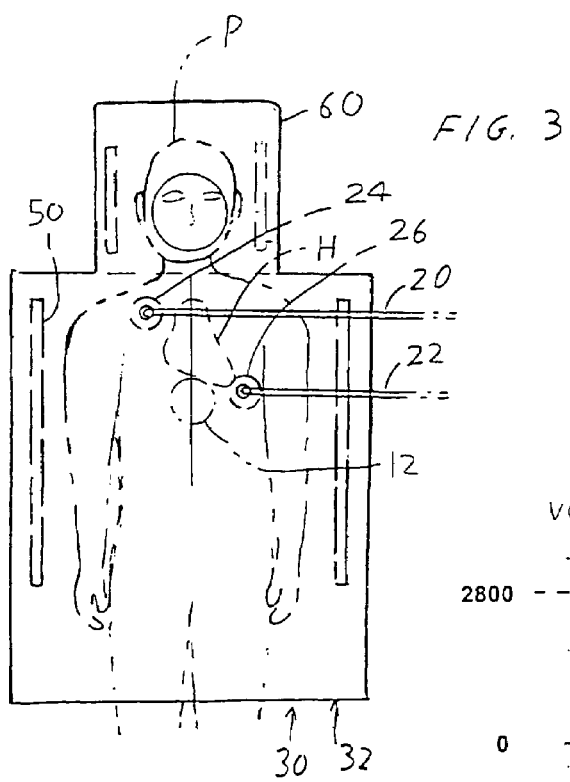
FIG. 3 is a plan view of the apparatus of the invention before its use with a victim, and also showing, in phantom lines, a victim over whom the apparatus is applies.

FIG. 3 shows the shape of the protective sheet 32 of the apparatus 30 relative to a victim P prior to placing the sheet on the victim. The sheet has a width of about 40 inches (30 to 55 inches) to readily extend across the width of most victims and preferably a few inches along the floor, without being cumbersome. In almost all cases, the sheet has an area of at least 200 cm$^2$ to cover at least the chest and area around the chest of the victim. It is possible to provide a protective sheet that covers only the area where the rescuer's hands press against the lower middle chest area, in which case the sheet could have an area as small as 150 cm$^2$.

In practice, applicant has found that when a defibrillation pulse, which may be up to a few thousand volts, is applied to the victim, that a rescuer who is pressing against the protective sheet (which does not have a conductive sandwiched sheet connected to the patient) feels a considerable shock. The shock is a voltage of perhaps two hundred volts although at very low amperage, which is not life threatening to the rescuer but which is very annoying. Applicant believes that the shock to the rescuer is due to a capacitive effect, where the sudden rise in voltage on the lower face of the protective sheet that touches the victim, results in passage of voltage to the rescuer by capacitive coupling. It is possible to use a thicker insulative sheet, which reduces the capacitive coupling, but this increases the weight of the sheet and makes it more cumbersome.

As mentioned above, applicant prefers a protective sheet such as shown at 100 in FIGS. 6 and 6A, with the layer 103 of electrically conductive material sandwiched between two layers 104, 106 of insulative or dielectric material. The materials are preferably highly flexible. The conductive layer 103 is connected through an extension 102 E, terminal part 108 and conductive adhesive 108A to the victim. Applicant finds that the presence of the electrically conductive layer 103 greatly reduces the shock felt by the rescuer who is touching the upper face of the sheet. Instead of a voltage of perhaps 200 volts felt by the rescuer, a voltage of perhaps 50 volts is felt by the rescuer, which, at very low current, is usually not highly annoying to the rescuer. It is possible to ground the conductive sheet 103 by a wire leading to a ground connection of the defibrillator, although this is generally more cumbersome.

Figure 7:
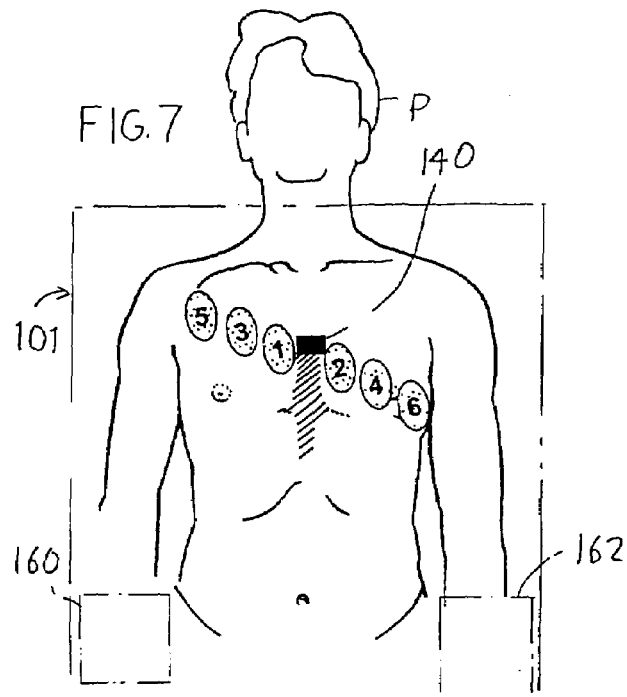
FIG. 7 shows, in phantom lines, a portion of a protective sheet of another embodiment of the invention, and shows, in solid lines, the placement of electrodes of the protective sheet in relation to the chest of a person being resuscitated.

FIG. 7 shows a protective sheet 101 that has six electrodes labeled 1, 2, 3, 4, 5, and 6, instead of only the two electrodes shown in FIG. 1. Although a defibrillation shock is applied only between two electrodes, the presence of six electrodes enables a choice as to which pair of electrodes to use for patients of different sizes. The distance between the centers of adjacent electrodes is at least 4 cm and is preferably at least 10 cm, to allow for optimal current path by choice of electrodes. The myocardial fibers tend to be aligned along a particular axis. Experiments have shown that, for a given electric field intensity, stimulation of the cells of the heart increase as the field intensity is more closely aligned with the long axes of the myocardial fibers. Electrodes are optimally spaced to provide the largest ventricular fibrillation amplitude. Accordingly, it is desirable to apply a defibrillation pulse between those pairs of electrodes which are spaced most closely parallel to the axes of the myocardial fibers to provide the largest VF amplitude. In actuality, one electrode will generally be located just below the patient's right clavicle and the second electrode will be located over the ribs on the patient's side in line with the axilla (armpit), and below the patient's left breast such as electrodes 5 and 6 in FIG. 7.

Figure 9:
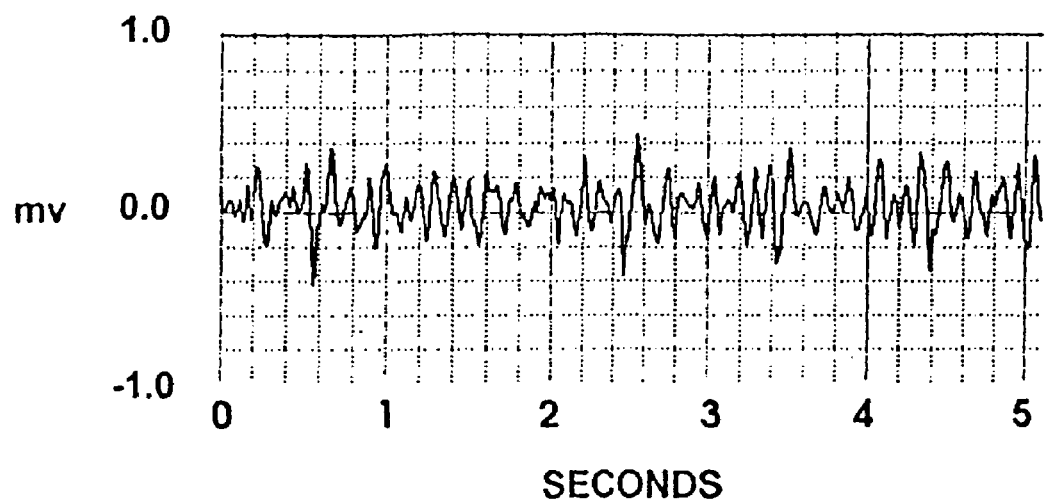
FIG. 9 is a graph showing a typical electrocardiogram of a victim, assuming that any noise from chest compressions is not present or has been filtered out.
Figure 10:
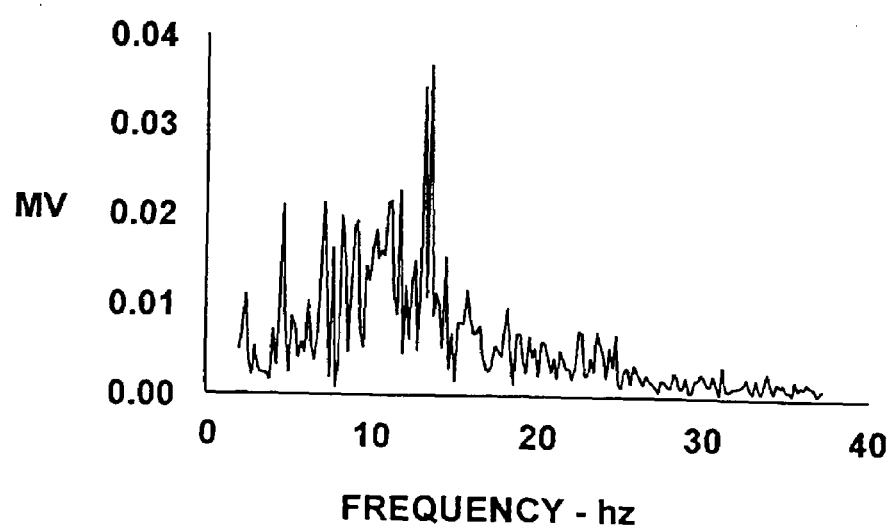
FIG. 10 is a graph showing variation of amplitude with frequency for the electrocardiogram of FIG. 9.

The preferred pair of electrodes are the pair where the EKG provides a highest probability of success from defibrillation. Applicant's earlier U.S. Pat. No. 5,957,856 and application Ser. No. 09/385,534 filed Aug. 30, 1999 mention that tests show that the probability of success is most closely correlated with the integral of amplitude with frequency of the Fourier transform of an EKG. FIG. 9 shows a typical EKG for a victim, showing the amplitude of heart signals in millivolts versus time in seconds. FIG. 10 shows the Fourier transform showing the amplitude in millivolts versus frequency in Hz. The integral of the graph of FIG. 10 which is the area under the graph (referred to as AMSA), is a good indicator of probability of success. Applicant takes the EKG from each of three pairs of electrodes, this being electrodes 1 and 2, electrodes 3 and 4, and electrodes 5 and 6 at the positions of FIG. 6. The integral of the Fourier transform for each EKG is then taken, and that pair of electrodes which results in the largest AMSA (integral of Fourier transform), is selected as the pair of electrodes between which a defibrillation pulse is applied.

The magnitude of the defibrillation voltage to be applied between the selected pair of electrodes must be determined. The amperage to be passed between the electrodes is generally about 30 to 40 amperes for a person having a weight of 75 kg (165 pounds). Human transthoric impedance has been reported to range from 15 to 150 ohms, with the average adult human impedance being about 70 to 80 ohms. It is noted that only a small fraction of delivered transthoric current reaches the heart, with the fraction being found to vary from about 0.1 to 0.4 depending on the patient's physical size. Applicant measures the impedance between the selected pair of electrodes, which is easily done by establishing a predetermined current such as 10 milliamperes at a frequency of 30 kHz and measuring the voltage across the selected electrodes. The voltage of the defibrillation pulse is then selected to be that which would result in a current flow of about 35 amperes. For example, if the impedance is found to be 75 ohms, then the maximum voltage of the defibrillation pulse will be 2,600 volts.

Figure 8:
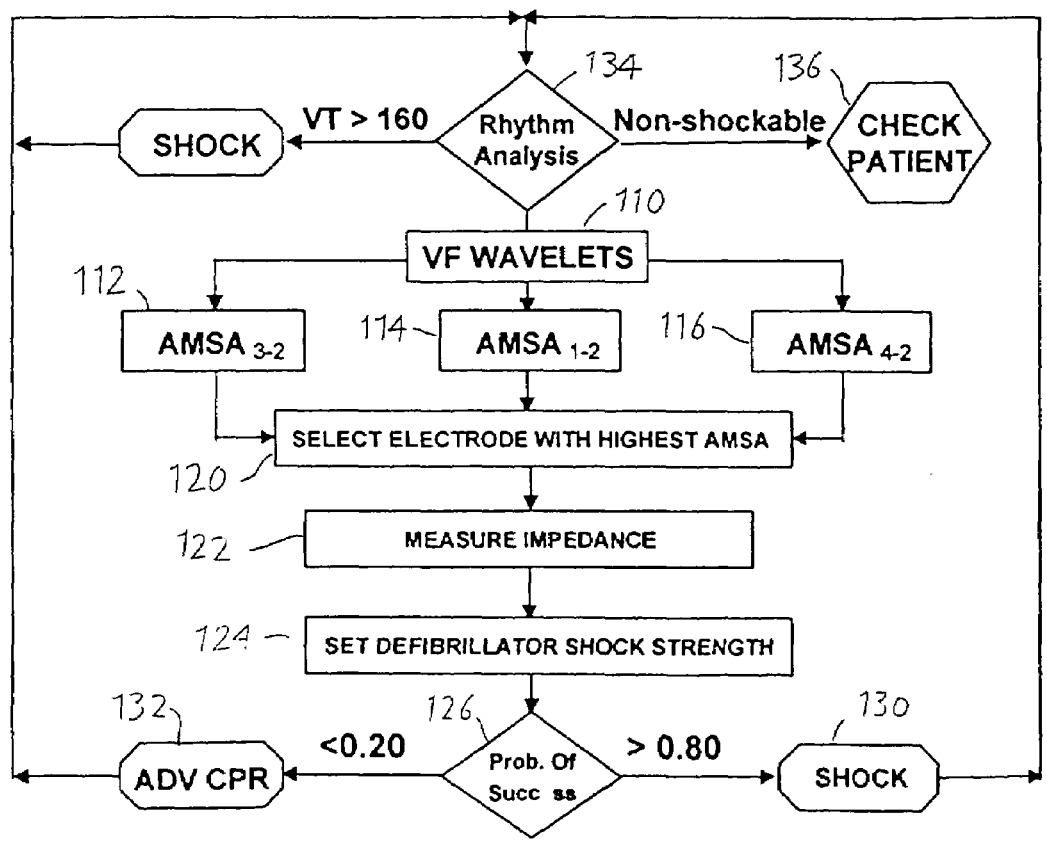
FIG. 8 is a block diagram showing a process in the use of the electrodes of the protective sheet of FIG. 7 to determine the optimum set of electrodes to which a defibrillation pulse can be applied, and to determine the preferred voltage of the pulse.

FIG. 8 is a block diagram showing the operation of applicant's defibrillator. First, VF wavelets from each of the three pairs of electrodes is received at 110. Then, the area under the Fourier transform of the amplitude versus frequency during a limited time period such as 5.0 seconds is determined for each of the three pairs of electrodes at 112, 114, and 116. Although it is possible to also calculate the probability of success, it is sufficient to just calculate the integral of the Fourier transform of the VF wavelets (ventricular fibrillation wavelet, which is the EKG signal of a person whose heart is fibrillation). A next step at 120 is to select the pair of electrodes that results in the greatest area under the graph. A next step at 122 is to measure the impedance of the victim between the selected pair of electrodes. A next step at 124 is to set the defibrillator shock strength, or voltage. A next step at 126 is to determine the probability of success of the defibrillation shock. In one case, at 130, the probability of success is determined to be more than eighty percent, and the defibrillator shock is applied to the patient. In another case, the probability of success is determined to be less than twenty percent, and a signal at 132 is applied to advise the rescuer that a defibrillator shock will not be applied, and to continue CPR (chest compressions and blowing of air into the patient's lung). If the probability of success is between twenty and eighty percent, then the rescuer has to make a decision as to whether or not to defibrillate, based on other factors. After the shock, at 134, a rhythm analysis is made to determine the regularity of the heartbeat. If the analysis indicates a regular heartbeat, then, at 136, the patient is merely checked. If VT (ventricular tachycardia) is above 160, then this indicates that another defibrillator shock would be desirable. However, applicant prefers, before each defibrillation shock, to analyze the wavelets 110 of the EKGs and perform the other steps indicated in FIG. 8.

Figure 11:
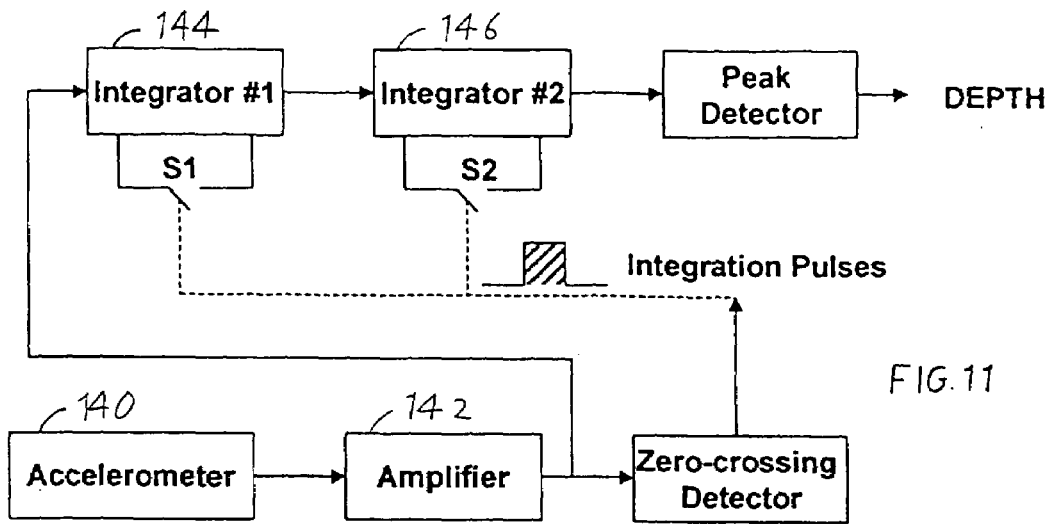
FIG. 11 is a block diagram showing how the output from an accelerometer on the protective sheet of FIG. 7 can be used to indicate the depth of a chest compression.

FIG. 7 shows a compression sensor at 140, which is at the middle of the chest, which is the area that is compressed in CPR. The sensor 140 is preferably an accelerometer. FIG. 11 is a block diagram showing that the output of the accelerometer 140 is amplified at 142, and two integrations are performed at 144 and 146. The first integration represents the velocity of the chest during a compression, while the second integration represents the distance traveled of the location that is compressed. The output of the second integrator 146, which indicates the depth of compression, can be compared to a preferred depth of compression, to indicate to the rescuer, whether the compression should be more or less forceful than the previous compression that he/she applied. Too great a compression can injure the patient, while too shallow a compression is not as effective in resuscitating the patient.

Figure 12:
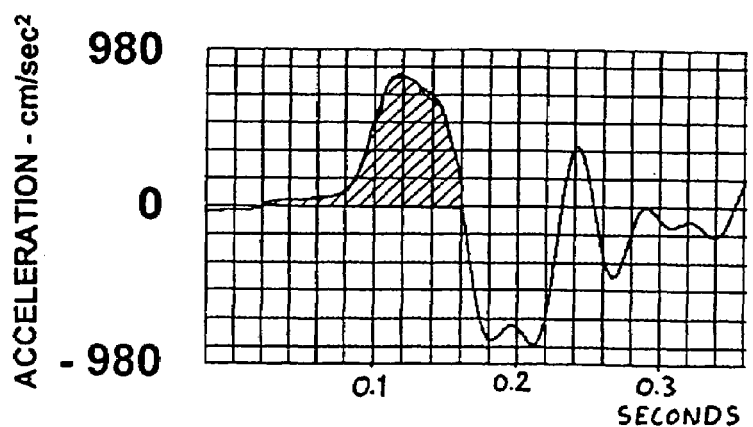
Figure 13:
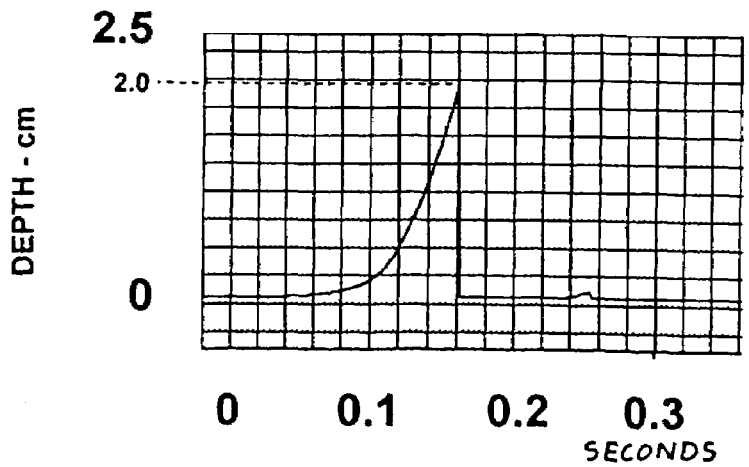
FIG. 13 is a graph showing the variation in output with time for the accelerometer of FIG. 11.

FIG. 12 is a graph showing variation in acceleration with time for a typical compression. The positive going acceleration represents the downward compression of the chest. FIG. 13 shows the second integration, which represents the depth of compression. A simple indicator can be used such as a red light that indicates that the compression is too vigorous, a yellow light to indicate that the compressions are not vigorous enough, and a green light to indicate the chest compressions are in the proper range.

FIG. 7 shows that the protective sheet 100 has pockets 160, 162. Such pockets can contain breathing valves and barriers that a rescuer can use to help protect himself from any diseases of the victim when applying mouth-to-mouth resuscitation, or a contact carbon dioxide sensor that senses carbon dioxide at a mucous membrane of the patient to indicate the condition of the patient. Such devices are often forgotten, and their presence in pockets of the protective sheet increases the chance that they will be available to the rescuer.

In the above discussion of FIGS. 8-10, applicant has mentioned that the area under the graph of FIG. 10 is a good indicator of the probability of success of defibrillation, and can be used to select a pair of electrodes between which a defibrillation shock is applied. Where ASA or AMSA represents the area under the graph, the probability of success is given by the following equation.

$$PS = \frac{e^{(0.32*ASA-0.64)}}{1+e^{(0.32*ASA-0.64)}}$$

It should be noted that there are other indications, mentioned in applicant's patent application Ser. No. 09/385,537 (and U.S. Pat. No. 5,957,856), including calculating the Fourier transform of power of the EKG (the current times the voltage) and using the highest PSA to indicate the pair of electrodes between which a defibrillation shock should be applied.

Thus, the invention provides an improved CPR system for resuscitating a victim or patient that has cardiac arrest symptoms. A protective sheet includes a layer of highly conductive material (e.g. a finely woven copper screen) sandwiched between layers of dielectric material, to further isolate the rescuer from high voltage shocks. The conductive layer is connected to a potential source that does not increase in voltage as much as the electrodes, such as directly to the patient's skin. The protective sheet can include pockets for holding important items that are likely to be forgotten by the rescuer. The protective sheet includes a plurality of sets of electrodes, and preferably three sets of electrodes to enable a selection of a pair of electrodes between which a defibrillation shock is applied. It is noted that the presence of three electrodes enables a choice of two different pairs (e.g. 1 and 2, 1 and 3, and 2 and 3), although applicant prefers at least four separate electrodes. A circuit selects the pair by analyzing heart signals or VF wavelets taken between each of the possible pairs of electrodes. In one circuit, the Fourier transform of the EKG signals is established, the area under a graph of voltage versus frequency is calculated, and that pair which results in the greatest value is selected as the pair between which the shock is applied. The impedance between the selected pair is measured, and the voltage to be applied is adjusted in order to apply a preselected current through the electrodes. A compression sensor such as an accelerometer or even a sensor that senses pressure to create a pressure-time relationship, is placed in the protective sheet, to indicate how vigorously the rescuer is applying chest compressions.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A kit for use by a rescuer who applies chest compressions to a victim that has cardiac arrest symptoms treatable by use of a defibrillator, comprising:

a protector sheet which has upper and lower faces and which resists the passage of current between said faces, said protector sheet being constructed to cover a chest area of the victim with the lower face resting directly against the victim and the upper face accessible to be pressed down by the rescuer;

said sheet having upper and lower dielectric layers forming said upper and lower faces and said sheet having a conductive layer of electrically conductive material lying between the dielectric layers;

said conductive layer occupying a majority of the area of said protector sheet upper face;

a connector extending from said conductive layer and having a termination part adapted for connecting to a potential source;

a pair of electrodes; and a defibrillator connected to said pair of electrodes with said pair of electrodes constructed so they can be placed against the skin of the victim.

2. Apparatus for use by a rescuer at a site where a victim with skin and a chest has cardiac arrest symptoms and is being treated by a defibrillator connected to electrodes lying against spaced electrode locations on the victim's chest, where the rescuer can press repeatedly against the middle of the victim's chest, the improvement comprising:

a protective sheet which includes upper and lower dielectric layers and a conductive layer between said dielectric layers, said lower dielectric layer having a lower face adapted to lie against the victim's chest and said upper dielectric layer having an upper face adapted to be repeatedly pressed down by the rescuer, said conductive layer having an area more than half the area of said upper face;

a connector which includes a conductor having an inner end connected to said conductive layer and an outer end adapted to connect to the skin of the patient;

a quantity of conductive adhesive lying on said conductor outer end and adapted to connect to the victim's skin.

3. A method for treating a victim that has a chest and that has cardiac arrest symptoms that are treatable by the use of a defibrillator, comprising:

connecting a pair of defibrillator electrodes of a defibrillator to the skin of the victim;

placing a protector sheet that has upper and lower dielectric layers forming upper and lower faces of the protector sheet, and having a conductive layer between the dielectric layers, against the victim so said lower face of the protective sheet lies against the chest of the victim and said upper face of the protective sheet is accessible to be pressed down by the rescuer;

electrically connecting said conductive layer to the skin of the victim at a location that is spaced at least 1.5 inches from the nearest one of said defibrillator electrodes;

repeatedly pressing down against said upper face of the protective sheet to produce chest compressions of the victim, and operating said defibrillator to apply electrical pulses to said defibrillator electrodes while conducting said step of repeatedly pressing down against said upper face of the protective sheet.

* * * * *